United States Patent
Glick et al.

(10) Patent No.: US 6,616,692 B1
(45) Date of Patent: Sep. 9, 2003

(54) INTRAOCULAR LENS COMBINATIONS

(75) Inventors: Robert E. Glick, Lake Forest, CA (US); Daniel G. Brady, San Juan Capistrano, CA (US)

(73) Assignee: Advanced Medical Optics, Inc., Santa Ana, CA (US)

(*) Notice: Subject to any disclaimer, the term of this patent is extended or adjusted under 35 U.S.C. 154(b) by 0 days.

(21) Appl. No.: 09/390,380

(22) Filed: Sep. 3, 1999

Related U.S. Application Data

(60) Provisional application No. 60/132,085, filed on Apr. 30, 1999.

(51) Int. Cl.[7] .................................................. A61F 2/16
(52) U.S. Cl. ....................................... 623/6.34; 623/6.37
(58) Field of Search ............................... 623/6.11, 6.22, 623/6.34, 6.37, FOR 105

(56) References Cited

U.S. PATENT DOCUMENTS

| | | |
|---|---|---|
| 1,483,509 A | 2/1924 | Bugbee |
| 2,129,305 A | 9/1938 | Feinbloom |
| 2,274,142 A | 2/1942 | Houchin |
| 2,405,989 A | 6/1946 | Beach |
| 2,511,517 A | 6/1950 | Spiegel |
| 3,031,927 A | 5/1962 | Wesley |
| 3,034,403 A | 5/1962 | Neefe |
| RE25,286 E | 11/1962 | DeCarle |
| 3,210,894 A | 10/1965 | Bentley et al. |
| 3,227,507 A | 1/1966 | Feinbloom |
| 3,339,997 A | 9/1967 | Wesley |
| 3,420,006 A | 1/1969 | Barnett |
| 3,431,327 A | 3/1969 | Tsuetaki |
| 3,482,906 A | 12/1969 | Volk |
| 3,542,461 A | 11/1970 | Girard et al. |

(List continued on next page.)

FOREIGN PATENT DOCUMENTS

| | | | |
|---|---|---|---|
| AU | 3225789 | 10/1989 | |
| DE | 2702117 | 7/1978 | |
| DE | 3246306 | 6/1984 | |
| DE | 195 01 444 A1 | * 7/1996 | ............ A61F/2/16 |
| DE | 195 01 444 | * 7/1996 | ............ A61F/2/16 |

(List continued on next page.)

OTHER PUBLICATIONS

Menzo et al. J Cataract Refract. Surg 24, Aug. 1998 (Published in U.S.), pp1039–1049.

Fechner et al. J Cataract Refract. Surg 24, Jan. 1998 (Published in U.S.), pp 48–56.

AMO Specs, Model AC–218, 1992 (Published in U.S.), 5 pages.

Chiron Vision, Nuvita MA20, 1997 (Chiron Vision Corp. 1997), 6 pages.

Thornton, Accommodation in Pseudophakia, 25, pp. 159–162.

(List continued on next page.)

*Primary Examiner*—David H. Willse
(74) *Attorney, Agent, or Firm*—Stout, Uxa, Buyan & Mullins, LLP; Frank J. Uxa; Peter Jon Gluck

(57) ABSTRACT

Intraocular lens combinations are provided which include a first optic having a negative optical power and being adapted to be placed in a substantially fixed position in a mammalian eye. A second optic having a higher optical power than the first optic is provided. In addition, a movement assembly is provided which is coupled to the second optic and is adapted to cooperate with the eye to effect accommodating movement of the second optic in the eye. Very effective accommodation is provided with the present intraocular lens combination. The present combinations can be effectively positioned to effectively inhibit or reduce the risk of posterior capsular opacification (PCO).

24 Claims, 2 Drawing Sheets

U.S. PATENT DOCUMENTS

| | | |
|---|---|---|
| 3,693,301 A | 9/1972 | Lemaltre |
| 3,922,728 A | 12/1975 | Krasnov |
| 3,932,148 A | 1/1976 | Krewalk, Sr. |
| 4,055,378 A | 10/1977 | Feneberg et al. |
| 4,062,629 A | 12/1977 | Winthrop |
| 4,162,122 A | 7/1979 | Cohen |
| 4,195,919 A | 4/1980 | Shelton |
| 4,199,231 A | 4/1980 | Evans |
| 4,210,391 A | 7/1980 | Cohen |
| 4,240,719 A | 12/1980 | Gullino et al. |
| 4,253,199 A | 3/1981 | Banko |
| 4,254,509 A | 3/1981 | Tennant |
| 4,274,717 A | 6/1981 | Davenport |
| 4,307,945 A | 12/1981 | Kitchen et al. |
| 4,315,673 A | 2/1982 | Guilino et al. |
| 4,316,293 A | 2/1982 | Bayers |
| 4,338,005 A | 7/1982 | Cohen |
| 4,340,283 A | 7/1982 | Cohen |
| 4,370,760 A | 2/1983 | Kelman |
| 4,377,329 A | 3/1983 | Poler |
| 4,402,579 A | 9/1983 | Poler |
| 4,404,694 A | 9/1983 | Kelman |
| 4,409,691 A | 10/1983 | Levy |
| 4,418,991 A | 12/1983 | Breger |
| 4,476,591 A | 10/1984 | Arnott |
| 4,504,982 A | 3/1985 | Burk |
| 4,551,864 A | 11/1985 | Akhavi |
| 4,560,383 A | 12/1985 | Leiske |
| 4,573,775 A | 3/1986 | Bayshore |
| 4,580,882 A | 4/1986 | Nuchman et al. |
| 4,596,578 A | 6/1986 | Kelman |
| 4,618,228 A | 10/1986 | Baron et al. |
| 4,618,229 A | 10/1986 | Jacobstein et al. |
| 4,636,049 A | 1/1987 | Blaker |
| 4,636,211 A | 1/1987 | Nielsen et al. |
| 4,637,697 A | 1/1987 | Freeman |
| 4,641,934 A | 2/1987 | Freeman |
| 4,676,792 A | 6/1987 | Praeger |
| 4,687,484 A | 8/1987 | Kaplan |
| 4,693,572 A | 9/1987 | Tsnetaki et al. |
| RE32,525 E | 10/1987 | Pannu |
| 4,702,244 A | 10/1987 | Mazzocco |
| 4,704,016 A | 11/1987 | DeCarle |
| 4,720,286 A | 1/1988 | Bailey et al. |
| 4,725,278 A | 2/1988 | Shearing |
| 4,752,123 A | 6/1988 | Blaker |
| 4,759,762 A | 7/1988 | Grendahl |
| 4,769,033 A | 9/1988 | Nordan |
| 4,790,847 A | 12/1988 | Woods |
| 4,813,955 A | 3/1989 | Achatz et al. |
| 4,830,481 A | 5/1989 | Futhey et al. |
| 4,842,601 A | 6/1989 | Smith |
| 4,881,804 A | 11/1989 | Cohen |
| 4,888,012 A | 12/1989 | Horn et al. |
| 4,888,015 A | 12/1989 | Domino |
| 4,890,912 A | 1/1990 | Visser |
| 4,890,913 A | 1/1990 | DeCarle |
| 4,892,543 A | 1/1990 | Turley |
| 4,898,461 A | 2/1990 | Portney |
| 4,906,246 A | 3/1990 | Grendahl |
| 4,917,681 A | 4/1990 | Nordan |
| 4,919,663 A | 4/1990 | Grendahl |
| 4,921,496 A | 5/1990 | Grendahl |
| 4,923,296 A | 5/1990 | Grendahl |
| 4,932,966 A | 6/1990 | Christie et al. |
| 4,932,968 A | 6/1990 | Caldwell et al. |
| 4,938,583 A | 7/1990 | Miller |
| 4,955,902 A | 9/1990 | Kelman |
| 4,976,534 A | 12/1990 | Milge et al. |
| 4,976,732 A | 12/1990 | Vorosmarthy |
| 4,990,159 A | 2/1991 | Kraff |
| 4,994,082 A | 2/1991 | Richards et al. |
| 5,000,559 A | 3/1991 | Takahashi et al. |
| 5,002,382 A | 3/1991 | Seidner |
| 5,019,098 A | 5/1991 | Mercier |
| 5,019,099 A | 5/1991 | Nordan |
| 5,047,052 A | 9/1991 | Dubroff |
| 5,071,432 A | 12/1991 | Baikoff |
| 5,089,024 A | 2/1992 | Christie et al. |
| 5,096,285 A | 3/1992 | Silberman |
| 5,112,351 A | 5/1992 | Christie et al. |
| 5,147,397 A | 9/1992 | Christ et al. |
| 5,158,572 A | 10/1992 | Nielsen |
| 5,166,711 A | 11/1992 | Portney |
| 5,166,712 A | 11/1992 | Portney |
| 5,171,266 A | 12/1992 | Wiley et al. |
| 5,173,723 A | 12/1992 | Volk |
| 5,192,317 A | 3/1993 | Kalb |
| 5,192,318 A | 3/1993 | Schneider et al. |
| 5,201,762 A | 4/1993 | Hauber |
| 5,225,858 A | 7/1993 | Portney |
| 5,258,025 A | 11/1993 | Fedorov et al. |
| 5,260,727 A | 11/1993 | Oksman et al. |
| 5,270,744 A | 12/1993 | Portney |
| 5,275,623 A | 1/1994 | Sarfarazi |
| 5,354,335 A | 10/1994 | Lipshitz et al. |
| 5,443,506 A | 8/1995 | Garabet |
| 5,476,514 A | 12/1995 | Cumming |
| 5,480,428 A | 1/1996 | Fedorov et al. |
| 5,489,302 A | 2/1996 | Skottun |
| 5,496,366 A | 3/1996 | Cumming |
| 5,521,656 A | 5/1996 | Portney |
| 5,562,731 A | 10/1996 | Cumming |
| 5,578,081 A | 11/1996 | McDonald |
| 5,607,472 A * | 3/1997 | Thompson ............... 623/6.13 |
| 5,628,795 A | 5/1997 | Langerman |
| 5,628,796 A | 5/1997 | Suzuki |
| 5,652,014 A | 7/1997 | Galin et al. |
| 5,652,638 A | 7/1997 | Roffman et al. |
| 5,657,108 A | 8/1997 | Portney |
| 5,674,282 A | 10/1997 | Cumming |
| 5,682,223 A | 10/1997 | Menezes et al. |
| 5,684,560 A | 11/1997 | Roffman et al. |
| 5,766,244 A | 6/1998 | Binder |
| 5,769,890 A | 6/1998 | McDonald |
| 5,776,191 A | 7/1998 | Mazzocco |
| 5,814,103 A | 9/1998 | Lipshitz et al. |
| 5,843,188 A | 12/1998 | McDonald |
| 5,876,442 A | 3/1999 | Lipshitz et al. |
| 6,013,101 A | 1/2000 | Israel |
| 6,096,078 A * | 8/2000 | McDonald ............... 623/6.22 |
| 6,176,878 B1 | 1/2001 | Gwon et al. |
| 6,217,612 B1 | 4/2001 | Woods |
| 6,488,708 B2 * | 12/2002 | Sarfarazi ............... 623/6.34 |

FOREIGN PATENT DOCUMENTS

| | | |
|---|---|---|
| EP | 0246216 | 11/1987 |
| EP | 0329981 | 8/1989 |
| EP | 0337390 | 10/1989 |
| EP | 0342895 | 11/1989 |
| EP | 0351471 | 1/1990 |
| EP | 0566170 | 10/1993 |
| EP | 0691109 | 1/1996 |
| EP | 0897702 | 2/1999 |
| GB | 2058391 | 4/1981 |
| GB | 2124500 | 2/1984 |
| GB | 2129155 | 5/1984 |
| GB | 2146791 | 4/1985 |
| GB | 2192291 | 1/1988 |
| GB | 2215076 | 9/1989 |
| JP | 2-126847 A * | 5/1990 ............. A61F/2/16 |

| | | |
|---|---|---|
| WO | 8603961 | 7/1986 |
| WO | 8700299 | 1/1987 |
| WO | 8707496 | 12/1987 |
| WO | 8902251 | 3/1989 |
| WO | 8911672 | 11/1989 |
| WO | 9416648 | 8/1994 |
| WO | 9503783 | 2/1995 |
| WO | 9615734 | 5/1996 |
| WO | 9625126 | 8/1996 |
| WO | 9743984 | 11/1997 |
| WO | 0134067 | 5/2001 |

OTHER PUBLICATIONS

Video Tape "New Elliptical Acco. IOL for Cataract Surgery", Shown at ASCRS Symposium on Apr. 10, 1999. (Video Enclosed).

Partial Program re: ASCRS Symposium, Showing Video Tape Shown Between Apr. 10–14, 1999.

* cited by examiner

INTRAOCULAR LENS COMBINATIONS

CROSS REFERENCE TO RELATED APPLICATION

This application claims the benefit of U.S. Provisional Application No. 60/132,085 filed Apr. 30, 1999.

BACKGROUND OF THE INVENTION

The present invention relates to intraocular lens combinations. More particularly, the invention relates to intraocular lens combinations which are adapted to provide substantial benefits, such as accommodating movement and/or inhibition of posterior capsule opacification (PCO) in the eye.

The human eye includes an anterior chamber between the cornea and iris, a posterior chamber, including by a capsular bag, containing a crystalline lens, a ciliary muscle, a vitreous chamber behind the lens containing the vitreous humor, and a retina at the rear of this chamber. The human eye has a natural accommodation ability. The contraction and relaxation of the ciliary muscle provides the eye with near, intermediate and distant vision. This ciliary muscle action shapes the natural crystalline lens to the appropriate optical configuration for focusing light rays entering the eye on the retina.

After the natural crystalline lens is removed, for example, because of cataract or other condition, a conventional, monofocal IOL can be placed in the posterior chamber. Such a conventional IOL has very limited, if any, accommodating ability. However, the wearer of such an IOL continues to require the ability to view both near and far (distant) objects. Corrective spectacles may be employed as a useful solution. Recently, multifocal IOLs without accommodating movement have been used to provide near/far vision correction.

Attempts have been made to provide IOLs with accommodating movement along the optical axis of the eye as an alternative to shape changing. Examples of such attempts are set forth in Levy U.S. Pat. No. 4,409,691 and several patents to Cumming, including U.S. Pat. Nos. 5,674,282 and 5,496,366. The disclosure of each of these patents is incorporated herein by reference.

One problem that exists with such IOLs is that they often cannot move sufficiently to obtain the desired accommodation. The degree of accommodation has been closely related to the lens prescription of the individual patient. In addition, the presence of such lenses can result in cell growth from the capsular bag onto the optics of such lenses. Such cell growth, often referred to as posterior capsule opacification (PCO), can interfere with the clarity of the optic to the detriment of the lens wearer's vision.

It would be advantageous to provide IOLs adapted for accommodating movement, which can preferably achieve an acceptable amount of accommodation and/or a reduced risk of

SUMMARY OF THE INVENTION

New intraocular lens combinations (ILCs) have been disclosed. The present ILCs provide distance, near and intermediate vision through position, preferably axial position, changes in the eye. The present combinations preferably enhance the degree of accommodation achieved in spite of the movement and space limitations within the eye. One advantage of the present ILCs is the ability to standardize the prescription or optical power of the moving or accommodating lens of the ILC. Thus, the required amount of movement in the eye to achieve accommodation can be substantially the same for all patients. This greatly facilitates the design of the moving or accommodating lens. Further, with at least certain of the present ILCs, inhibition of PCO is obtained. The present ILCs are relatively straight-forward in construction, can be implanted or inserted into the eye using systems and procedures which are well known in the art and function effectively with little or no additional treatments or medications being required.

In one broad aspect of the present invention, intraocular lens combinations (ILCs) comprise a first optic, second optic and a movement assembly. The first optic has a negative optical power and is adapted to be placed in a substantially fixed position in a mammalian eye. The second optic has a higher optical power than the first optic. The movement assembly is coupled to the second optic and is adapted to cooperate with the eye, for example, the zonules, ciliary muscle and capsular bag of the eye, to effect accommodating movement of the second optic in the eye.

Advantageously, the second optic has a high plus optical power to reduce the amount of movement, for example, axial movement, in the eye needed to provide accommodation for intermediate and near vision. The negative or minus optical power of the first optic compensates for the excess plus or positive optical power in the first optic. The use of such a compensating lens, that is the first optic having a negative optical power, can allow, for standardization of the optical power correction in the second optic. In other words, the optical power of the second optic, that is the movable optic, can be approximately equal from optic to optic, while the optical power of the first optic, that is the fixed optic, is adjusted from optic to optic to meet the specific vision correction needs (prescription) of each individual patient. Consequently, the required amount of movement of the second optic in the eye can be approximately the same for all patients.

The present ILCs provide accommodation, preferably an acceptable degree of accommodation, in spite of movement and space limitations in the eye. For example, the maximum theoretical amount of axial movement for a simple disc lens having an overall diameter of 11 millimeters (mm) and an optic diameter of 5 mm that undergoes 1 mm of compression in its diameter is about 1.65 mm. The amount of axial movement required for a plus 15 diopter optic to provide 2.5 diopters of additional power in the spectacle plane is about 2.6 mm. However, a plus 30 diopter optic requires only 1.2 mm of axial movement to provide 2.5 diopters of additional power in the spectacle plane. Thus, by increasing the plus power of the second optic, which is adapted for accommodating movement, a reduced amount of movement is needed to achieve higher or enhanced degrees of accommodation. The first or fixed optic preferably has a minus power to compensate for the excess plus power in the second optic.

The present ILCs preferably include first and second optics with optical powers which provide a net plus optical power. To illustrate, assume that the patient requires a plus 15 diopter correction. The first optic is provided with a minus 15 diopter optical power and the second optic with a plus 30 diopter optical power. The net optical power of this ILC is approximately the sum of minus 15 diopters and plus 30 diopters or plus 15 diopters, the desired prescription for the patient in question. The powers of the first and second optics are only approximately additive since the net power of the combination also depends on other factors including, but not limited to, the separation of the two optics, the magnitude of the power of each individual optic and its location in the eye and the like factors. Also, by adjusting the optical power of the first optic, the net optical power of the ILC can be adjusted or controlled even though the optical power of the second optic is standardized or remains the same, for example, at a plus 30 diopter optical power. By standardizing the optical power of the second optic, the amount of movement in the eye required to obtain a given level of accommodation is substantially the same, and preferably well within the space limitations in the eye, from patient to patient.

In one very useful embodiment, the movement assembly comprises a member including a proximal end region coupled to the second optic and a distal end region extending away from the second optic and adapted to contact a capsular bag of the eye. Such movement assembly may completely circumscribe the second optic or may be such as to only partially circumscribe the second optic.

The second optic preferably is adapted to be positioned in the capsular bag of the eye.

The first optic may be coupled to a fixation member, or a plurality of fixation members, adapted to assist in fixating the first optic in the eye. Each fixation member preferably has a distal end portion extending away from the first optic. In one embodiment, the distal end portion of the fixation member is adapted to be located in the capsular bag of the eye. Alternately, the distal end portion of the fixation member may be located in contact with a sulcus of the eye. As a further alternate, the distal end portion of the fixation member may be adapted to be located in an anterior chamber of the eye.

The first optic may be located posterior in the eye relative to the second optic or anterior in the eye relative to the second optic. In a useful embodiment, the first optic is adapted to be positioned in contact with the posterior wall of the capsular bag of the eye. This positioning of the first optic provides for effective compensation of the plus or positive vision correction power of the second optic. In addition, by having the first optic in contact with the posterior wall of the capsular bag, cell growth from the capsular bag onto the ILC, and in particular onto the first and second optics of the ILC, is reduced. This, in turn, reduces the risk of or inhibits posterior capsule opacification (PCO).

In one embodiment, the fixation member or members and the movement assembly are secured together, preferably permanently secured together. Thus, when inserting the ILC into the eye, a single combined structure can be inserted. This reduces the need to position the first and second optics relative to each other. Put another way, this feature allows the surgeon to very effectively and conveniently position the ILC in the eye with reduced surgical trauma to the patient.

The fixation member and movement assembly may be secured, for example, fused, together at the distal end portion of the fixation member and the distal end region of the movement assembly.

In another broad aspect of the present invention, ILCs are provided which comprise a first optic having a posterior surface adapted to be positioned in contact with a posterior wall of the capsular bag of the eye; a second optic adapted to focus light toward a retina of the eye; and a movement assembly coupled to the second optic and adapted to cooperate with the eye to effect accommodating movement of the second optic in the eye. The first optic has a substantially plano optical power or a negative optical power. These ILCs are particularly adapted to inhibit PCO.

The first optic of these combinations preferably is adapted to be placed in a substantially fixed position in the eye. The posterior surface of the first optic advantageously is configured to substantially conform to a major portion, that is, at least about 50%, of the posterior wall of the capsular bag of the eye in which the combination is placed. More preferably, the posterior surface of the first optic is configured to substantially conform to substantially all of the posterior wall of the capsular bag. Such configuration of the first optic is very useful in inhibiting cell growth from the eye onto the first and second optics and in inhibiting PCO.

In one embodiment, the first optic has a substantially plano optical power and the second optic has a far vision correction power. In an alternate embodiment, the first optic has a negative optical power and the second optic has a positive optical power, more preferably, so that the optical powers of the first and second optics provide a net plus optical power in the eye in which the combination is placed.

In a very useful embodiment, the first optic includes an anterior surface and at least one projection extending anteriorly from this anterior surface. The at least one projection is positioned to limit the posterior movement of the second optic in the eye. Thus, the movement of the second optic is effectively controlled to substantially maintain the configuration of the combination and/or to substantially maintain an advantageous spacing between the first and second optics.

The movement assembly may be structured and functions similarly to movement assembly of the previously described ILCs.

The first optic may have a fixation member or members coupled thereto. The fixation member or members are adapted to assist in fixating the first optic in the eye, that is in contact with the posterior wall of the capsular bag of the eye. In one embodiment, the first optic itself is configured and/or structured so that no fixation member or members are needed to maintain the first optic in contact with the posterior wall of the capsular bag of the eye. The first optic and the movement assembly of these ILCs may be secured together.

In general, the first and second optics of the present ILCs may be made of any suitable materials. Preferably, the first and second optics are made of polymeric materials. More preferably, the first and second optics and the movement assembly, and the fixation member(s), if any, are deformable for insertion through a small incision in the eye.

The present movement assemblies are sufficiently flexible to facilitate movement of the second optic in the eye upon being acted upon by the eye. In one very useful embodiment, the movement assembly includes a hinge assembly, preferably adapted and positioned to facilitate the accommodating movement of the second optic.

In those embodiments in which the first optic has a substantially plano optic power, the second optic preferably has a far vision correction power, more preferably such a power for infinity, in the unaccommodated state.

In a further broad aspect of the present invention, methods for inserting an ILC in an eye are provided. Such methods comprise providing an ILC in accordance with the present invention, as described herein. The ILC is placed into the eye, for example, in the capsular bag of the eye or partly in the capsular bag of the eye, using equipment and techniques which are conventional and well known in the art. The ILC is placed in a rest position in the eye, for example, a position so that the eye, and in particular the ciliary muscle and zonules of the eye, effectively cooperate with the movement assembly to move the second optic of the ILC anteriorly in the eye from the rest position to provide for positive accommodation. No treatments or medications, for example, to paralyze the ciliary muscle, to facilitate fibrosis or otherwise influence the position of the ILC in the eye, are required.

Preferably, the first and second optics and the movement assembly are deformed prior to being placed into the eye. Once the ILC is placed in the eye, and after a normal period of recovery from the surgical procedure, the ILC, in combination with the eye, provides the mammal or human wearing the ILC with effective accommodation, preferably with reduced risk of PCO. In the unaccommodated state, the ILC preferably provides the mammal or human wearing the ILC with far vision correction.

Any and all features described herein and combinations of such features are included within the scope of the present invention provided that the features of any such combination are not mutually inconsistent.

Further aspects and advantages of the present invention are set forth in the following detailed description and claims, particularly when considered in conjunction with the accompanying drawings in which like parts bear like reference numerals.

DETAILED DESCRIPTION OF THE DRAWINGS

Figure 1:
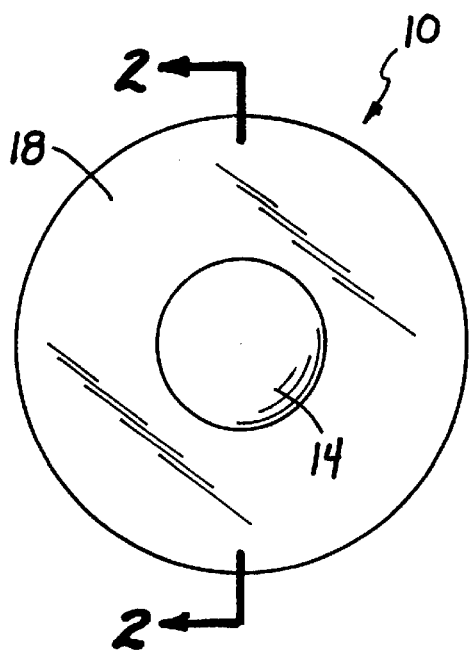
FIG. 1 is a front plan view of an ILC in accordance with the present invention.
Figure 2:
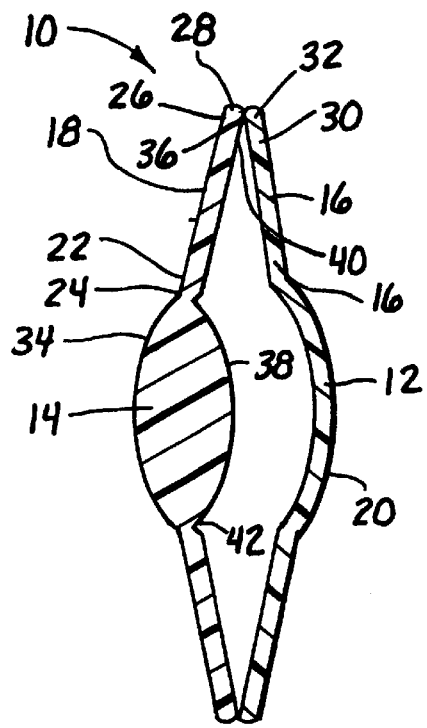
FIG. 2 is a cross-sectional view taken generally along line 2—2 of FIG. 1.

Referring now to FIGS. 1 and 2, an ILC according to the present invention, shown generally at 10, includes a first optic 12, a second optic 14, a disc type fixation member 16 and a disc type movement assembly 18.

The first optic 12 has substantially plano optical power and is adapted to be held in a fixed position, for example, at least partially by the fixation member 16. When the ILC 10 is positioned in a human eye, the posterior surface 20 of first optic 12 is in contact with the inner posterior wall of the capsular bag of the eye. This positioning of optic 12 is very effective in reducing or inhibiting endothelial cell growth from the capsular bag onto the first optic 12. In effect, the positioning of the first optic 12 against the posterior surface of the capsular bag inhibits or reduce the risk of PCO.

The second optic 14 includes a distance vision correction power. The movement assembly 18 extends radially outwardly from second optic 14 and fully circumscribes the second optic 14. Movement assembly 18 has a proximal end region 22 which is coupled to the second optic 14 at first optic periphery 24.

Movement assembly 18 extends radially outwardly to a distal end region 26 including a peripheral zone 28.

Fixation member 16 includes a distal end portion 30 including a peripheral area 32. The movement assembly 18 and fixation member 16 are fused together at the peripheral zone 28 and peripheral area 32. Thus, the entire ILC 10 is a single unitary structure. The first optic 12 and fixation member 16 can be manufactured separately from second optic 14 and movement assembly 18 and, after such separate manufacture, the fixation member and movement assembly can be fused together. Alternately, the entire ILC 10 can be manufactured together. Also, if desired, the first optic 12 and fixation member 16 can be inserted into the eye separately from the second optic 14 and movement assembly 18. Thus, ILC 10 can comprise a plurality of separate components.

Movement assembly 18 extends outwardly from second optic 14 sufficiently so that the distal end region 26, and in particular the peripheral zone 28 of the distal end region, is in contact with the inner peripheral wall of the posterior capsular bag when the ILC 10 is implanted in the eye.

As best seen in FIG. 2, when ILC 10 is at rest, the second optic 14 is positioned vaulted anteriorly relative to the distal end region 26 of movement assembly 18. In other words, the anterior surface 34 of second optic 14 is anterior of the anterior surface 36 of movement assembly 18 at distal end region 26 and/or the posterior surface 38 of the second optic 14 is anterior of the posterior surface 40 of the movement assembly at the distal end region.

The first and second optics 12 and 14 may be constructed of rigid biocompatible materials, such as polymethyl methacrylate (PMMA), or flexible, deformable materials, such as silicone polymeric materials, acrylic polymeric materials, hydrogel polymeric materials, and the like, which enable the optics 12 and 14 to be rolled or folded for insertion through a small incision into the eye. Although the first and second optics 12 and 14 as shown are refractive lens bodies, the present ILCs can include at least one diffractive lens body, and such embodiment is included within the scope of the present invention.

As noted previously, first optic 12 has a substantially plano or zero optical power. Second optic 14 is prescribed for the wearer of ILC 10 with a baseline or far (distance) diopter power for infinity. Thus, the wearer of ILC 10 is provided with the vision correction power of second optic 14 with little or no contribution from the first optic 12.

The fixation member 16 and movement assembly 18, as shown, are integral (unitary) with and circumscribe the first and second optics 12 and 14, respectively. Alternately, fixation member 16 and/or movement assembly 18 can be mechanically or otherwise physically coupled to first optic 12 and second optic 14, respectively. Also, the fixation member 16 and/or movement assembly 18 may only partially circumscribe first and second optics 12 and 14, respectively, and such embodiments are included within the scope of the present invention. The fixation member 16 and movement assembly 18 may be constructed from the same or different biocompatible materials as first and second optics 12 and 14, and preferably are made of polymeric materials, such as polypropylene silicone polymeric materials, acrylic polymeric materials, and the like. Movement assembly 18 has sufficient strength and rigidity to be effective to transfer the force from the ciliary muscle of the eye so that the second optic 14 is movable axially in the eye to effect accommodation.

Movement member 18 includes a region of reduced thickness 42 located at the proximal end region 22. This area of reduced thickness, which completely circumscribes the second optic 14, acts as a hinge to provide additional flexibility to the movement member 18 to extenuate or amplify the accommodating movement of second optic 14 in response to the action of the ciliary muscle and zonules.

The fixation member 16 and movement assembly 18 preferably are deformable, in much the same manner as first and second optics 12 and 14 are deformable, to facilitate passing ILC 10 through a small incision into the eye. The material or materials of construction from which fixation member 16 and movement assembly 18 are made are chosen to provide such members with the desired mechanical properties, e.g., strength and/or deformability, to meet the needs of the particular application involved.

The ILC 10 can be inserted into the capsular bag of a mammalian eye using conventional equipment and techniques, for example, after the natural crystalline lens of the eye is removed, such as by using a phacoemulsification technique. The ILC 10 preferably is rolled or folded prior to insertion into the eye, and is inserted through a small incision into the eye and is located in the capsular bag of the eye.

The ILC 10 in the eye is located in a position in the capsular bag so that the posterior surface 20 of first optic 12 is maintained in contact with the inner posterior wall of the capsular bag. As noted previously, positioning the first optic 12 in contact with the posterior wall of the capsular bag reduces the risk of or inhibits cell growth from the capsular bag onto the first optic 12 which, in turn, reduces or inhibits PCO. The ciliary muscle and zonules of the eye provide force sufficient to move axially second optic 14 sufficiently to provide accommodation to the wearer of ILC 10.

The ILC 10 should be sized to facilitate the movement of the second optic 14 in response to the action of the ciliary muscle and zonules of the eye in which the ILC is placed.

If the ILC 10 is too large, the ciliary muscle and zonules will be inhibited from effectively contracting/relaxing so that the amount of accommodating movement will be unduly restricted. Of course, if the ILC 10 is too small, the second optic 14 will be ineffective to focus light on the retina of the eye, may cause glare and/or the movement member may not cooperate with the eye to effect the desired amount of accommodating movement. If the ILC 10 is to be included in an adult human eye, the first and second optics 12 and 14 preferably have diameters in the range of about 3.5 mm to about 7 mm, more preferably in the range of about 5 mm to about 6 mm. The ILC 10 preferably has an overall maximum diameter, with the movement assembly 18 in the unflexed or rest state, in the range of about 8 mm to about 11 mm or about 12 mm.

The present ILC 10 has the ability, in cooperation with the eye, to move the second optic 14 both posteriorly and anteriorly in the eye, to provide for both distance focus and near focus, respectively. This movement of ILC 10 advantageously occurs in response to action of the ciliary muscle and zonules, which action is substantially similar to that which effects accommodation in an eye having a natural crystalline lens. Thus, the ciliary muscle and zonules require little, if any, retraining to function in accordance with the present invention. The movement member 18, as described herein, preferably is effective to facilitate or even enhance or extenuate the axial movement of the second optic 14 caused by the action of the ciliary muscle and zonules to provide increased degree of accommodation.

Figure 3:
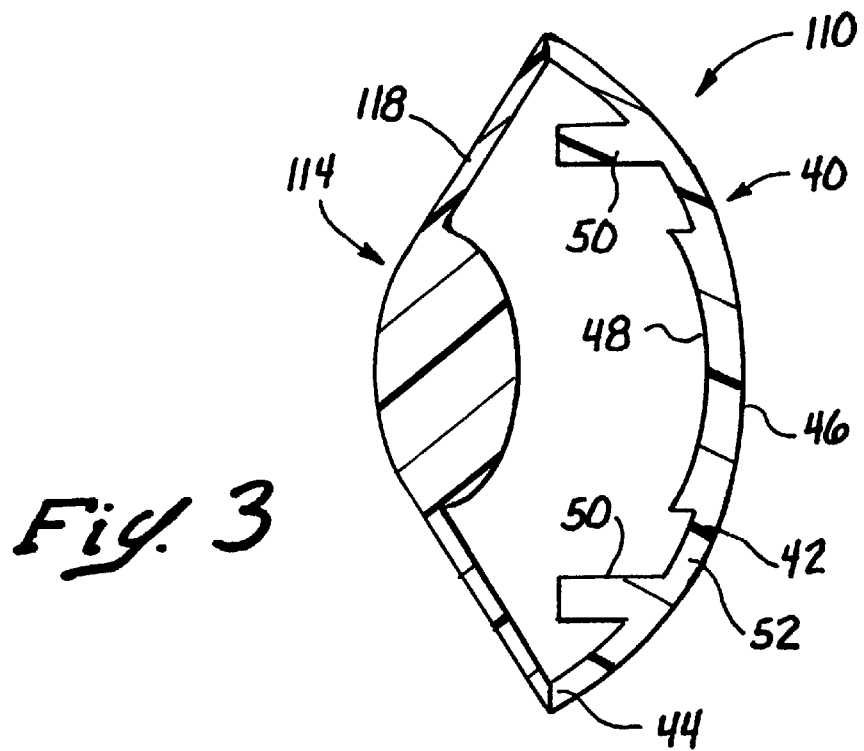
FIG. 3 is a cross-sectional view of an additional ILC in accordance with the present invention.

FIG. 3 illustrates an additional ILC, shown generally at 110, in accordance with the present invention. Except as expressly described herein, ILC 110 is structured and functions similar to ILC 10. Components of ILC 110 which correspond to components of ILC 10 are indicated by the same reference numeral increased by 100.

One primary difference between ILC 110 and ILC 10 relates to the substitution of a posterior lens structure 40 for the first optic 12 and fixation member 16. Lens structure 40 includes a posterior face 42 which is configured to come in contact with and substantially conform to the inner posterior surface of the capsular bag of the eye in which the ILC 110 is to be placed. Thus, the surface 42 which extends around the peripheral area 44 and across the center region 46 of the lens structure 40 is adapted to come in contact with and substantially conform to the inner posterior wall of the capsular bag. Moreover, the lens structure 40 is adapted to remain in contact with this inner posterior wall of the capsular bag and to be fixed in the eye. This configuration has been found to be very effective in inhibiting cell growth from the eye onto the ILC 110. The anterior surface 48 of lens structure 40 is configured to provide the lens structure with a substantially plano or zero optical power. Second optic 114 is prescribed for the wearer of ILC 110 with a baseline or distance or far (distance) dioptic power for infinity. Thus, the wearer of ILC 110 is provided with a vision correction power of second optic 114 with little or no contribution from the lens structure 40.

Alternately, second optic 114 has a high plus power, for example, plus 30 diopters. The lens structure 40, and in particular the region of the lens structure, defined by the anterior surface 48, which extends substantially across the entire field of vision of the wearer of ILC 110, has a minus vision correction power which is controlled to provide the correction prescription for use in the eye in which the ILC 110 is placed. For example, if this eye requires: a plus 15 diopter power, the lens structure 40 has a vision correction power of approximately minus 15 diopters so that the net vision correction power of the combination of lens structure 40 and second optic 114, is plus 15 diopters.

The lens structure can be made from materials described previously with regard to first optic 12 and fixation member 16.

One additional feature of lens structure 40 relates to the anteriorly extending projections 50 which extend from the base element 52 of lens structure 40. The number of these projections 50 can range from 2 to about 6 or more. Alternately, a continuous annulus projecting anteriorly can be provided. The purpose of the projections 50 or the continuous annulus is to limit the posterior movement of the second optic 114 and movement assembly 118. This limitation in the movement provides an additional degree of control of the ILC 110, and prevent a collapse of the ILC 110 and maintains an advantageous degree of separation between second optic 114 and anterior surface 48 of lens structure 40.

Figure 4:
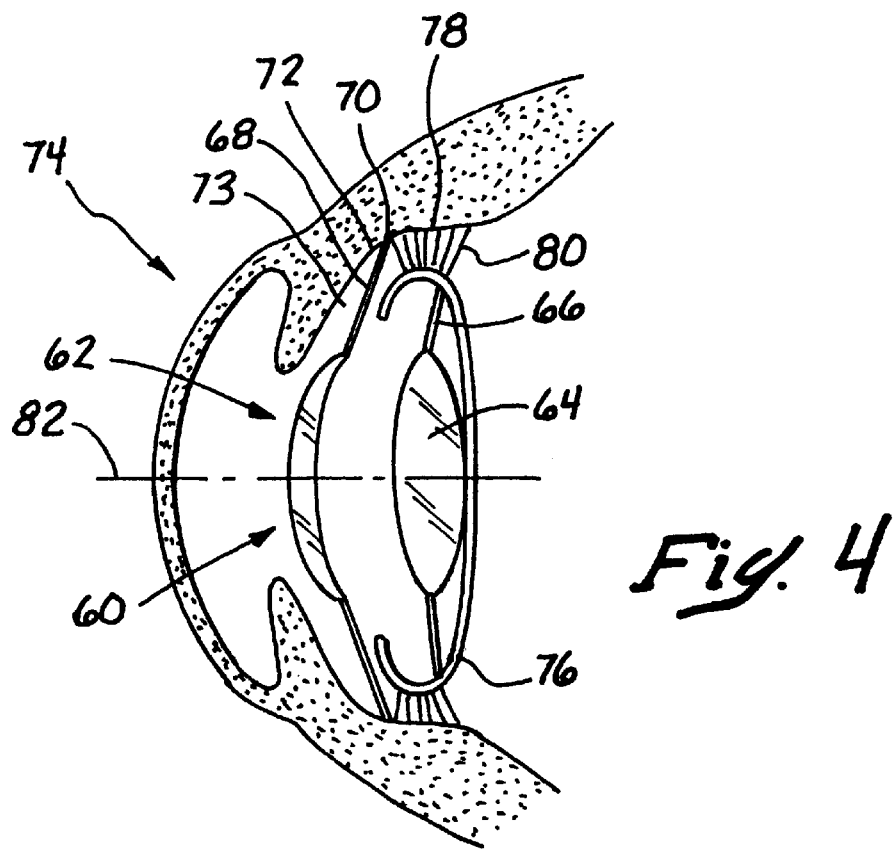
FIG. 4 is a fragmentary sectional view of an eye in which an alternate ILC in accordance with the present invention has been implanted.

FIG. 4 illustrates the use of an alternate ILC in accordance with the present invention. This ILC, shown generally at 60 includes a first optic 62, a second optic 64 and a movement assembly 66. First optic 62 is coupled to a fixation member 68 which includes a distal end portion 70 in contact with the periphery 72 of the sulcus 73 of eye 74. Fixation member 68 is a disk fixation member which completely circumscribes the first optic 62. However, it should be noted that the disc fixation member 68 can be replaced by two or more filament fixation members or plate fixation members or other types of fixation members, many of which are conventional and well known in the art. Movement assembly 66 is coupled to second optic 64 and completely circumscribes the second optic. Second optic 64 is located in the capsular bag 76 of eye 74 and is vaulted anteriorly to some extent to enhance accommodating movement of the second optic.

Second optic 64 has a high plus power, for example, plus 30 diopters. The first optic 62 is a compensating negative or minus lens having a minus vision correction power which is controlled to provide the correct prescription for use in eye 74. For example, if the eye 74 requires a plus 15 diopter power, the first optic has a vision correction power of approximately minus 15 diopters so that the net vision correction power of the combination of first optic 62 and second optic 64 is plus 15 diopters. The first optic 62, fixation member 68, second optic 64 and movement assembly 66 can be made from materials described previously with regard to the first optic 12, fixation member 16, second optic 14 and movement assembly 18, respectively.

In the configuration shown in FIG. 4, the fixation member 68 is in contact with the periphery 72 of the sulcus 73 of the eye 74. This is a relatively durable component of the eye and is effective to support the fixation member 68 in maintaining the first optic 62 in a fixed position.

The movement assembly 66 cooperates with the ciliary muscle 78 and zonules 80 of eye 74 to move the second optic 64 axially along optical axis 82 of the eye.

Figure 5:
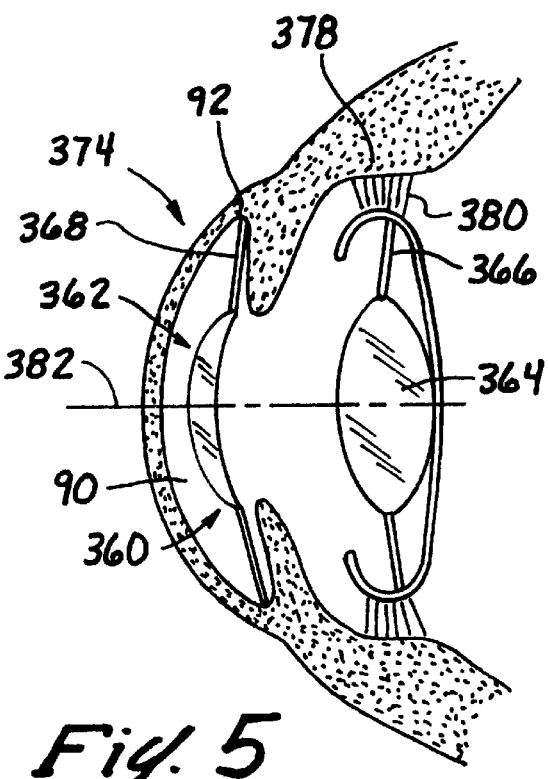
FIG. 5 is a fragmentary sectional view of an eye in which another ILC in accordance with the present invention has been implanted.

FIG. 5 illustrates another ILC, shown generally at 360, in accordance with the present invention. Except as expressly described herein, ILC 360 is structured and functions similarly to ILC 60. Components of ILC 360 which correspond to components of ILC 60 are identified by the same reference numeral increased by 300.

One primary difference between ILC 360 and ILC 60 relates to the positioning of first optic 362. Specifically, first optic 362 is located in anterior chamber 90 of eye 374. Fixation member 368 is coupled to the first optic 362 and extends outwardly and comes in contact with the angle 92 of eye 374. The arrangement of first optic 362 and fixation member 368 is such that the first optic is maintained in a substantially stationary position in the anterior chamber 90 of eye 374. The second optic 364 is adapted to be moved axially along optical axis 382 of eye 374 by the ciliary muscle 378 and zonules 380 acting on the movement assembly 366.

Figure 6:
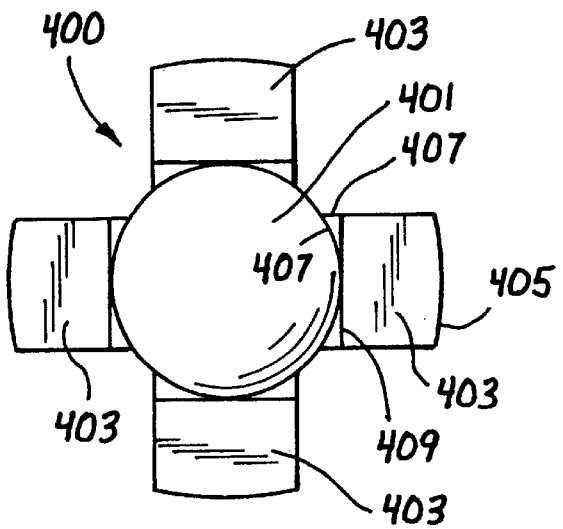
FIG. 6 is a front plan view of an intraocular lens useful in an ILC in accordance with the present invention.

FIG. 6 illustrates a still further embodiment of an intraocular lens in accordance with the present invention. This intraocular lens, shown generally at 400 includes an optic 401 and four (4) equally spaced apart movement members 403. Each of the movement members 403 includes a distal region 405 and a proximal region 407 which is coupled to the optic 401. A hinge, for example, a linear hinge, such as a reduced thickness area 409, is located near the proximal end 407 of each of the movement members 403. A linear hinge is particularly advantageous to achieve enhanced, or even substantially maximum theoretical, axial movement.

The IOL 400 can be used in place of the various second optic/movement assembly subcombinations noted above. One distinction between IOL 400 and these other subcombinations is the use of four (4) individual movement members 403 which do not totally circumscribe the optic 401 relative to the movement assemblies noted previously which fully circumscribe the second optics. It should be noted that the movement assemblies of the present ILCs can have other configurations, for example, which are effective to facilitate or even enhance the movement of the second optics.

While this invention has been described with respect to various specific examples and embodiments, it is to be understood that the invention is not limited thereto and that it can be variously practiced within the scope of the following claims.

What is claimed is:

1. A system of intraocular lens combinations for a plurality of patients each requiring different vision corrections, comprising:

one of a plurality of the same high plus power optics configured to cooperate with the eye and provide accommodation; and one of a plurality of optics each having a different negative power than the others and being configured to maintain a substantially fixed axial position after implantation in a patient's eye;

wherein the optical powers of the high plus power and negative power optic in any one combination provide a net plus power to the combination, and wherein a magnitude of the negative power optic of any one combination is selected based on the required vision correction for a particular patient.

2. The system of claim 1, wherein the high plus power optics are configured to be implanted in the capsular bag of the eye.

3. The system of claim 2, wherein at least one of the plurality of negative power optics is configured to be implanted in the capsular bag of the eye in a location that is posterior with respect to the high plus power optic.

4. The system of claim 1, wherein at least one of the plurality of negative power optics is configured to be implanted in contact with the sulcus of the eye.

5. The system of claim 1, wherein at least one of the plurality of negative power optics is configured to be implanted in the anterior chamber of the eye.

6. The system of claim 1, wherein at least one of the plurality of negative power optics is coupled to a fixation member which includes a distal end portion configured to contact a surrounding anatomical structure in the eye.

7. The system of claim 6, wherein the fixation member is a disk fixation member which completely circumscribes the negative power optic.

8. The system of claim 6, wherein the fixation member comprises two or more members selected from the group consisting of:

filament fixation members; and plate fixation members.

9. The system of claim 1, further including a movement assembly coupled to each of the high plus power optics, the movement assembly being configured to cooperate with the eye to effect accommodating axial movement of the high plus power optic.

10. The system of claim 6, wherein each movement assembly comprises individual movement members which do not totally circumscribe the respective high plus power optic and include a proximal region coupled to the optic and a distal region configured to contact a surrounding anatomical structure in the eye.

11. The system of claim 10, wherein each of the individual movement members includes a hinge located near the proximal region.

12. The system claim 11, wherein the hinge comprises an area of reduced thickness in the movement member.

13. The system of claim 1, wherein the high plus power is more than about 15 diopter.

14. The system of claim 13, wherein the high plus power is about 30 diopter.

15. An intraocular lens combination, comprising:

a negative power optic configured to maintain a substantially fixed axial position after implantation in the capsular bag of a patient's eye; and a plus power optic formed and implanted separately from the negative power optic and configured to be implanted in the capsular bag of the eye in an anterior position relative to the negative power optic, the plus power optic configured to provide accommodation.

16. The system of claim 15, wherein the negative power optic is coupled to a fixation member which includes a distal end portion configured to contact the surrounding capsular bag.

17. The system of claim 16, wherein the fixation member is a disk fixation member which completely circumscribes the negative power optic.

18. The system of claim 16, wherein the fixation member comprises two or more members selected from the group consisting of:

filament fixation members; and plate fixation members.

19. The system of claim 15, further including a movement assembly coupled to the plus power optic, the movement assembly being configured to cooperate with the capsular bag to effect accommodating axial movement of the plus power optic.

20. The system of claim 19, wherein the movement assembly comprises individual movement members which do not totally circumscribe the plus power optic and include a proximal region coupled to the optic and a distal region configured to contact the surrounding capsular bag.

21. The system of claim 20, wherein each of the individual movement members includes a hinge located near the proximal region.

22. The system claim 21, wherein the hinge comprises an area of reduced thickness in the movement member.

23. The system of claim 15, wherein the plus power is more than about 15 diopter.

24. The system of claim 23, wherein the plus power is about 30 diopter.

* * * * *

UNITED STATES PATENT AND TRADEMARK OFFICE
CERTIFICATE OF CORRECTION

PATENT NO. : 6,616,692 B1
DATED : September 9, 2003
INVENTOR(S) : Robert E. Glick and Daniel G. Brady It is certified that error appears in the above-identified patent and that said Letters Patent is hereby corrected as shown below:

Column 1,
Line 56, after the word "of." please insert -- PCO. --

Column 8,
Line 26, delete colon after the word "requires."

Column 10,
Line 44, replace "6" with -- 9 --.
Line 63, delete "and implanted".
Line 64, after the word "be" insert -- separately --.

Signed and Sealed this

Twentieth Day of July, 2004

JON W. DUDAS
*Acting Director of the United States Patent and Trademark Office*